United States Patent [19]

Johnson et al.

[11] 4,275,906
[45] Jun. 30, 1981

[54] PRESSURE SENSITIVE RECORDING SHEETS

[75] Inventors: Grannis S. Johnson, Plainfield; Ira M. Rose, Millburn, both of N.J.

[73] Assignee: Diamond Shamrock Corporation, Dallas, Tex.

[21] Appl. No.: 58,563

[22] Filed: Jul. 18, 1979

[51] Int. Cl.³ .................... B41M 5/16; B41M 5/22
[52] U.S. Cl. .................... 282/27.5; 106/21; 427/150; 428/307; 428/537; 428/914
[58] Field of Search .................... 106/21; 252/316; 282/27.5; 427/150, 151; 428/307, 914, 537, 913

[56] References Cited

U.S. PATENT DOCUMENTS

| | | | |
|---|---|---|---|
| 2,710,849 | 6/1955 | Siggel | 260/40 |
| 3,836,383 | 9/1974 | Kiritani et al. | 282/27.5 X |
| 3,936,566 | 2/1976 | Sato et al. | 428/323 |
| 3,968,320 | 7/1976 | Herber et al. | 427/150 X |
| 3,996,405 | 12/1976 | Porter | 282/27.5 |
| 4,130,299 | 12/1978 | Wygant | 282/27.5 |
| 4,147,830 | 4/1979 | Kato et al. | 428/324 |
| 4,159,208 | 6/1979 | Hayashi et al. | 428/307 X |

FOREIGN PATENT DOCUMENTS 1142338  1/1963  Fed. Rep. of Germany ............... 8/93

*Primary Examiner*—Bruce H. Hess
*Attorney, Agent, or Firm*—Neal T. Levin

[57] ABSTRACT

Pressure sensitive recording sheets are prepared characterized by containing on one side thereof color former dissolved in a solvent which is one or a mixture of alkoxy diphenyl alkanes having the following structure:

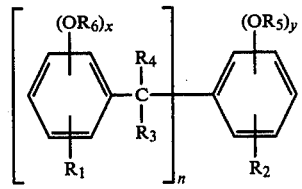

where $R_1$, $R_2$, $R_3$ and $R_4$ are H or a straight or branched chain alkyl group of 1 to 8 carbon atoms and can be the same or different; $R_5$ is a straight or branched chain alkyl group of 1 to 9 carbon atoms; $R_6$ is a straight or branched chain alkyl group of 1 to 8 carbon atoms; x is 0, 1 or 2; y is 1 or 2 and n is 1 or 2, with the proviso that the sum of the carbon atoms in $R_1$, $R_2$, $R_3$, $R_4$, $R_5$ and $R_6$ does not exceed 9 and with the further proviso that where the alkoxy diphenyl alkane is a solid to viscous liquid, at least one diluent or at least one other generally liquid solvent or mixture thereof is present. The treated side of the sheet is brought into contact with a developer. Upon application of pressure, color is produced by reaction between the color former and the developer.

20 Claims, No Drawings

PRESSURE SENSITIVE RECORDING SHEETS

BACKGROUND OF THE INVENTION

1. Field of the Invention

This invention relates to pressure sensitive recording sheets.

2. Description of the Prior Art

Pressure sensitive record materials are known. For example, a first sheet, generally paper, is treated on one side with a coating of microcapsules containing a solution of color former. A second sheet is treated on one side with a developer (coreactant material) such as acidic clay or polymeric material. When the coated side of both sheets are brought into contact with each other and pressure applied to the first sheet, e.g., by pencil, pen or typewriter, the microcapsules are ruptured and the color former is released and comes into contact with the second sheet containing the developer. A color is produced by reaction between the color former and the developer.

Several disclosures relating to pressure sensitive recording paper which are particularly directed to the selection of the solvent for the color former are set forth below.

U.S. Pat. No. 3,836,383—Kiritani et al—Sept. 17, 1974 discloses as the solvent two alkyl substituted benzene nuclei connected by $-C_nH_{2n}-$ and $-CH(CH_3)-$.

U.S. Pat. No. 3,936,566—Sato et al—Feb. 3, 1976 discloses as the solvent the reaction product of styrene and alkyl substituted aromatic hydrocarbons.

U.S. Pat. No. 4,130,299—Wygant—Dec. 19, 1978 discloses benzylated xylenes as the solvent.

One of the problems confronting the art is the selection of the solvent for the color former. A number of criteria relating to the selection of the solvent in manufacture of pressure sensitive paper are:

The solvent must dissolve the color former.

The solvent must have reduced viscosity.

The solvent must be non-toxic.

The solvent must have minimal odor.

The solvent must not inhibit color development.

As the art has demonstrated, there is no one universal or completely acceptable solvent. All, to some degree have undesirable properties such as toxicity, odor, inhibition of color development, etc. Further, as pointed out in U.S. Pat. No. 4,130,299 there still remains a lack of understanding of routes to odor improvement. This is borne out by the fact that the prior art has approached the problem by depending upon modifications of the solvent which are position isomers or which introduce additional alkyl groups on known hydrocarbon moieties.

SUMMARY OF THE INVENTION

Pressure sensitive recording sheets are prepared wherein the color former is dissolved in a solvent which is one or a mixture of alkoxy diphenyl alkanes having the following structure:

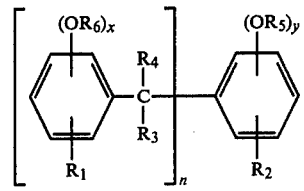

where $R_1$, $R_2$, $R_3$ and $R_4$ are H or a straight or branched chain alkyl group of 1 to 8 carbon atoms and can be the same or different; $R_5$ is a straight or branched chain alkyl group of 1 to 9 carbon atoms; $R_6$ is a straight or branched chain alkyl group of 1 to 8 carbon atoms; x is 0, 1 or 2; y is 1 or 2 and n is 1 or 2, with the proviso that the sum of the carbon atoms in $R_1$, $R_2$, $R_3$, $R_4$, $R_5$ and $R_6$ does not exceed 9 and with the further proviso that where the alkoxy diphenyl alkane is a solid to viscous liquid, at least one diluent or at least one other generally liquid solvent or mixture thereof is present. Where the various R substituents are alkyl, they may be straight or branched chain such as methyl, ethyl, n-propyl, isopropyl, n-butyl, isobutyl, secondary butyl, tertiary butyl, n-pentyl, neopentyl, hexyl, heptyl, 2-ethyl hexyl, n-octyl or nonyl.

Although not critical, there can be dissolved in the solvent from about 1 percent by weight to about 10 percent by weight, usually from about 2 percent by weight to about 5 percent by weight, of the color former based on the weight of the solvent. The solution of color former, e.g., in the form of microcapsules, is applied to one surface of a sheet, which surface is brought into contact with the surface of a second sheet containing the developer. Alternatively the first sheet which is coated with the color former is further coated with the developer. In both cases, upon the application of pressure, e.g., by pencil, pen or typewriter, the color former is released, e.g., by rupture of the microcapsules, so that it comes into contact with the developer whereupon color is produced.

DESCRIPTION OF THE PREFERRED EMBODIMENTS

The Solvent

The solvents for the color former are one or a mixture of alkoxy diphenyl alkanes having the following structure:

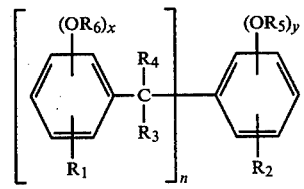

where $R_1$, $R_2$, $R_3$ and $R_4$ are H or a straight or branched chain alkyl group of 1 to 8 carbon atoms and can be the same or different; $R_5$ is a straight or branched chain alkyl group of 1 to 9 carbon atoms; $R_6$ is a straight or branched chain alkyl group of 1 to 8 carbon atoms; x is 0, 1 or 2; y is 1 or 2 and n is 1 or 2, with the proviso that the sum of the carbon atoms in $R_1$, $R_2$, $R_3$, $R_4$, $R_5$ and $R_6$ does not exceed 9 and with the further proviso that where the alkoxy diphenyl alkane is a solid to viscous liquid, at least one diluent or at least one other generally liquid solvent or mixture thereof is present. Where the various R substituents are alkyl, they may be straight or branched chain such as methyl, ethyl, n-propyl, isopropyl, n-butyl, isobutyl, secondary butyl, tertiary butyl, n-pentyl, neopentyl, hexyl, heptyl, 2-ethyl hexyl, n-octyl or nonyl.

Examples of alkoxy diphenyl alkanes are one or a mixture of: the methyl ether of styrenated phenol; the methyl ether of distyrenated phenol; the n-butyl ether of styrenated phenol; the n-butyl ether of distyrenated phenol; the n-propyl ether of styrenated phenol; the methyl ether of alpha methyl styrenated phenol; 2-methoxy diphenyl methane (m.p. 29°–30° C.); 4-methoxy diphenyl methane; 4-ethoxy diphenyl methane; 4-methoxy-2-methyl diphenyl methane; 2-ethyl-4-benzyl anisole; 1-phenyl-1-(o-methoxytolyl) ethane; 1-phenyl-1-(m-methoxytolyl) ethane (m.p. 63° C.); 1-phenyl-1-(2-methoxyphenyl) propane; 1-phenyl-1 (2-methoxyphenyl) ethane (m.p. 26° C.); bis (2-methoxyphenyl) methane (m.p. 66° C.); 2-methoxyphenyl-4'-methoxyphenyl methane (m.p. 26°–28° C.); bis (4-methoxyphenyl) methane (m.p. 51°–53° C.); bis (2-ethoxyphenyl) methane (m.p. 84°–85° C.); 2-ethoxyphenyl-4'-ethoxyphenyl methane (m.p. 60°–63° C.); bis (4-ethoxyphenyl) methane (m.p. 38° C.); bis (4-methoxy-2-methylphenyl) methane (m.p. 69° C.); bis (4-methoxy-3-methylphenyl) methane (m.p. 24° C.); bis (6-methoxy-3-methylphenyl) methane (m.p. 55° C.); bis (6-methoxy-3-propylphenyl) methane (m.p. 51° C.); 6,4'-dimethoxy-3-methyldiphenyl methane (m.p. 74° C.); 1,1-bis (4-methoxyphenyl) ethane (m.p. 59.4°, 72° C.); 1,1-bis (4-methoxyphenyl) propane (m.p. 44° C.); 2,2-bis (4-methoxyphenyl) propane (m.p. 59°–61.5° C.); 2,2-bis (4-ethoxyphenyl) propane (m.p. 49°–50° C.); 2,2-bis (4-propoxyphenyl) propane; 1,1-bis (4-methoxyphenyl) butane; 2-ethyl-1,1-bis (4-methoxyphenyl) butane; 3-methyl-1,1-bis (4-methoxyphenyl) butane; 1,1-bis (4-methoxyphenyl) heptane; 1,1-bis (6-methoxy-3-methylphenyl) ethane.

This class of compounds has been found to be uniquely effective as solvents for the color former. Whereas it would be expected that a compound having a phenolic hydroxyl such as styrenated phenol would be useful since the presence of the phenolic hydroxyl would raise the boiling point, thereby reducing the vapor pressure and reducing odor, such compound is not desirable. This is because the phenolic hydroxyl would react with the color former. Further, the phenolic character itself is responsible for undesirable odor, toxicity and increased viscosity. Thus, the transformation of the phenolic moiety to an ether moiety removes the undesirable properties attributable to the phenolic moiety while retaining its desirable properties. That is, the undesirable phenolic odor is eliminated and replaced by a more tolerable ether odor, the reactivity with the color former has been eliminated by blocking the phenolic hydroxyl and the viscosity is reduced. Another advantage of the use of alkoxy diphenyl alkanes as solvents is that where the solution of color former and solvent has water present such as the water present from the encapsulation procedure, the solvent vapor pressure is reduced by hydrogen bonding of water with the ether oxygen of the solvent. This brings about a reduction of odor. Water can be present in an amount up to the solubility limit of the water in the solution of solvent and color former.

With respect to the alkoxy diphenyl alkane solvents odor is usually more acceptable with those solvents having lower vapor pressures. Lower vapor pressure is usually associated with higher molecular weights.

The alkoxy diphenyl alkanes can be prepared by known methods, many of these compounds and their preparations being reported in the literature. Where the alkoxy diphenyl alkanes are prepared in part from styrene or alpha methyl styrene, the following two routes can be employed.

One route involves reaction between styrene or alpha-methyl styrene and phenol or cresol (ortho, meta, para or mixtures) in the presence of an acid catalyst to form styrenated phenol or substituted styrenated phenol. Usually, the styrene and the phenol or cresol are reacted in a mole ratio of about 1 to 2:1 to 4. This is followed by alkylation of the styrenated phenol to give the corresponding ether. Alkylation (ether formation) can be achieved by reaction of the styrenated phenol with alkyl halides or alkyl sulfates in the presence of sodium hydroxide. Useful alkyl halides are methyl chloride, ethyl chloride, primary or secondary propyl chloride and primary, secondary, iso-or tertiary butyl chloride. Useful alkyl sulfates are dimethyl sulfate and diethyl sulfate. Ether formation can also be achieved by the acid catalyzed addition of styrenated phenol to olefins such as ethylene, propylene, isobutylene, butene-1, pentenes, hexenes and heptenes.

Alternatively, the phenol or cresol can be converted to the ether derivative by either of the alkylation procedures described above. The resulting ether is then reacted with styrene or alpha-methyl styrene.

The pressure-sensitive recording sheets utilizing the improved solvents of the present invention may be prepared according to well-known, conventional procedures. Descriptions of methods for preparing the first sheet which contains the color former and the second sheet containing the developer or the single sheet containing both color former and developer on the same side of the sheet or containing the color former and developer on opposite sides of the same sheet are to be found in the literature and such methods do not constitute a part of the present invention. Similarly, formation and application of microcapsules of color former and solvent or color former and solvent dispersed in a binder onto a sheet is fully disclosed in the literature. The solvents of this invention replace the conventional solvents in order to produce improved pressure-sensitive copying systems.

It must be recognized that some of the alkoxy diphenyl alkanes are solids to viscous liquids. However, in many instances, preparation without purification generally will yield liquid materials. Be that as it may, alkoxy diphenyl alkanes which are liquids at room temperature may be used alone, with diluents or even with known solvents which are generally liquids or with mixtures of the foregoing. Alkoxy diphenyl alkanes which are solids, semisolids or viscous liquids at room temperature must be used in combination with another generally liquid solvent which can be alkoxy diphenyl alkane or known solvent or with diluents or with mixtures of the foregoing in order to provide a mixture having the requisite degree of liquidity for use in pressure-sensitive recording systems.

For purposes of this invention the term "diluent" includes inert or substantially inert materials which are of little practical use alone as dye solvents, either because they have poor solvating power for the color former or because they act in some way to inhibit the development of color. Further, a diluent should not be selected which worsens the odor. For example, one part by weight of alkoxy diphenyl alkane may be admixed with from 0 to about three parts by weight of diluent for each part of solvent. Where the alkoxy diphenyl alkane is solid to viscous liquid, the minimum amount of diluent is that amount required to provide the requisite degree of liquidity. Useful diluents are one or a mixture of mineral or vegetable oils, such as kerosene, paraffin oil, mineral spirits, neatsfoot oil, sperm oil, lard oil, olive oil, soybean oil, cottonseed oil, coconut oil, or rapeseed oil, or an organic aryl compound such as aromatic naphtha or $C_{1-12}$ alkyl benzene. Monoalkylbenzene mixtures, sometimes called "alkylates", are particularly useful as diluents with dye solvents of this invention. Such alkylates are commercially available as intermediates for the manufacture of anionic liquid and solid detergents. Typical is a mono-$C_{10}$ to $C_{15}$ alkylbenzene mixture.

The diluents referred to herein function to alter physical properties of the solvent such as viscosity or vapor pressure as may be desired for handling or processing considerations or for imparting the requisite degree of liquidity. The diluents may also serve to reduce the total cost of the solvent in the system.

The solvents may also contain certain additives specifically intended to alter or control the final properties of the fluid, as for example viscosity control agents, vapor pressure control agents, freezing point depressants, antioxidants, and the like.

Where known solvents are used with either the liquid or the solid to viscous liquid alkoxy diphenyl alkane solvents, the properties of the of the known solvents are improved depending upon the amount of alkoxy diphenyl alkane present.

The total quantity of known solvent plus alkoxy diphenyl alkane when used with the color former should fall within the ranges heretofore set for the alkoxy diphenyl alkane alone.

The Color Former

The solvents of the present invention are utilized in combination with one or more color formers of normally colorless form. Color formers which react with the developer to produce color when used in the present invention are not especially limited and any conventional color former can be employed. Representative examples of these color formers are: triarylmethane compounds such as 3,3-bis (p-dimethylaminophenyl)-6-dimethylaminophthalide, i.e., Crystal Violet Lactone, 3,3-bis(p-dimethylaminophenyl)phthalide, 3-(p-dimethylaminophenyl)-3-(1,2-dimethyl indol-3-yl) phthalide, 3-(p-dimethylaminophenyl)-3-(2-methylindol-3-yl)phthalide, 3-(p-dimethylaminophenyl)-3-(2-phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazole-3-yl)-5-diimethylaminophthalide, 3,3-bis(2-phenylindol-3-yl)-5-dimethylaminophthalide, 3-p-dimethylaminophenyl-3-(1-methylpyrol-2-yl)-6-dimethylaminophthalide, and the like; diphenylmethane compounds such as 4,4'-bis-dimethylaminobenzhyrin benzyl ether, N-halo-(e.g., iodo-, chloro-, bromo-)phenyl-leucoauramine, N-2,4,5-trichlorophenyl leucoauramine, and the like; xanthene compounds such as Rhodamine B-anilinolactam, Rhodamine B-p-nitroanilinolactam, Rhodamine B-p-chloroanilinolactam, 7-dimethylamino-2-methoxyfluoran, 7-diethylamino-2-methoxyfluoran, 7-diethylamino-3-methoxyfluoran, 7-diethylamino-3-chlorofluoran, 7-diethylamino-3-chloro-2-methylfluoran, 7-diethylamino-2,2-dimethylfluoran, 7-diethylamino-3-acetylmethylaminofluoran, 7-diethylamino-3'-methylaminofluoran, 3,7-diethylaminofluoran, 7-diethylamino-3-dibenzylamino fluoran, 7-diethylamino-3-methylbenzylaminofluoran, 3-diethylamino-7-phenylamino-6-methylfluoran, 7-diethylamino-3-chloroethylmethylaminofluoran, 7-diethylamino-3-diethylaminofluoran, and the like; thiazine compounds such as benzoyl leuco methylene blue, p-nitrobenzoylleuco methylene blue, and the like; spiro compounds such as 3-methyl-spiro-dinaphthopyran, 3-ethyl-spiro-dinaphthopyran, 3,3'-dichloro-spiro-dinaphthopyran, 3-benzylspiro-dinaphthopyran, 3-methyl-naphtho-(3-methoxy-benzo)-spiro-pyran, 3-propyl-spiro-dibenzopyran, and the like, and mixtures thereof.

The color formers listed above produce color when the color former is brought into contact with acidic developers. Of course, other color formers that produce color by other mechanisms can be used as well. It is only necessary that the appropriate developer is used.

Developer

The developer or coreactant material can be any conventional material useful for this purpose. Useful developers for the preceding color formers are acidic materials such as acidic clays and acidic polymeric materials. Examples are inorganic acidic materials such as bentonite, zinc oxide, kaolin, clay, active clay, acid clay, zeolite, bentonite, attapulgite, talc, colloidal silica, etc. and acidic polymers such as phenolaldehyde resin, maleic acid-rosin, hydrolysis product of styrenemaleic anhydride copolymers, hydrolysis product of ethylenemaleic anhydride copolymer, carboxypolyethylene, hydrolysis product of vinyl methyl ether-maleic anhydride copolymer, etc.

Of course, other developers which employ other methods of developing color in a color former can be used as well. It is only necessary that the appropriate color former is used.

Recording Sheets

Pressure sensitive recording sheets are well-known in the art and the present invention is not limited to any specific form of or preparation of same. That is, the color former can be microencapsulated or dispersed in a binder by known means and applied to a support such as a sheet which can be paper, resin coated paper or plastic. The developer can be applied as an outer layer to the same or applied to a different support or sheet which is positioned with its developer side against the color former. Alternatively the color former and developer can be applied to opposite sides of the same sheet as in the case where a plurality of sheets are used together. Here, the color former on one sheet is positioned against the developer of another sheet.

Suitable procedures for preparing pressure sensitive recording sheets are taught in U.S. Pat. No. 2,548,366 (Apr. 10, 1951), U.S. Pat. No. 2,712,507 (July 5, 1955), U.S. Pat. No. 2,730,456 (Jan. 10, 1956), U.S. Pat. No. 2,800,457 (July 23, 1957), U.S. Pat. No. 3,041,289 (June 26, 1962) and U.S. Pat. No. 4,076,887 (Feb. 28, 1978).

For a fuller understanding of this invention, reference may be made to the following examples. The examples are given merely to illustrate the invention and are not to be construed in a limiting sense. In the examples, all percents are percent by weight.

EXAMPLE I

Preparation of the methyl ether of styrenated phenol

A 60 gallon stainless steel reactor, equipped with impeller, condenser, receiver and splitter was charged with 302.7 pounds (2.8 moles) of anisole. The reactor was blanketed with nitrogen. Borontrifluoride etherate, 1.7 pounds was then charged into the reactor. Temperature of the reactor was raised to 120° C. Styrene, 145.6 pounds (1.4 moles) was pumped into the reactor during 1–2 hours while maintaining temperature at 120°–125° C. This temperature was held until a refractive index (25° C.) of 1.5490 was attained indicating that all of the styrene had reacted. The reactor was cooled to 90° C. Then 1.4 pounds of 28% aqueous ammonia were charged to the reactor. The equipment was set for vacuum distillation and unchanged anisole was distilled off at 4–5 inches pressure while heating to 160° C. The reactor was maintained under vacuum at 160° C. for one-half hour. 159 Pounds of anisole was collected. Live steam was applied under vacuum for 1 hour to remove traces of anisole. Steam was shut off and the reactor was maintained under vacuum at 160° C. for one-half hour to dry the product. The reactor was then cooled to room temperature and the contents filtered through a 12 plate, plate and frame stainless steel filter press. Yield of product was 249 pounds having a refractive index, 25° C., 1.5760 and viscosity, 25° C., 20 centipoises.

Analysis of product by gas chromatography indicated the following:

63.6% Monostyrenated anisole (Methyl ether of styrenated phenol) composed of three isomers (o, m and p).

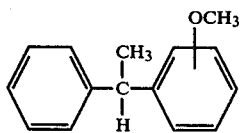

33.4% Distyrenated anisole (Methyl ether of distyrenated phenol).

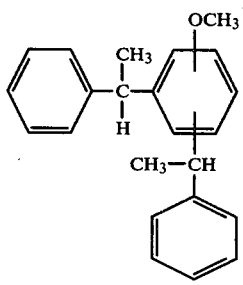

3.0% higher condensates.

EXAMPLE II

Preparation of the n-butyl ether of styrenated phenol

Styrenated phenol, 500 grams (2.5 moles), which was principally a mixture of 80–82% by weight monostyrenated phenol (a mixture of 2-(1-phenyl ethyl) phenol, 3-(1-phenyl ethyl) phenol and 4-(1-phenyl ethyl) phenol), and 18–20% by weight of distyrenated phenol were charged into a steel reactor equipped with stirrer, thermometer, dropping funnel and distilling head connected to a condenser. Temperature of the reactor was raised to 130° C. Then 140 grams (2.5 moles) of potassium hydroxide as a 45% aqueous solution was added dropwise while allowing water to distill off. After addition of potassium hydroxide, the temperature was allowed to rise to 150° C. and maintained until water no longer distilled off. The condenser was then set for reflux. N-butyl chloride, 233 grams (2.5 moles), was added dropwise while maintaining temperature at 150° C. Temperature at 150° C. was maintained until analysis for potassium hydroxide was below 0.5%. The reactor was cooled to 90° C. and contents filtered. 465 Grams of a mobile liquid product was obtained having a refractive index, 25° C., 1.5527, viscosity, 25° C., 30 centipoises and as determined by gas chromatography composed chiefly of approximately 80 to 82% by weight of 2- and 4-(1-phenyl ethyl) butoxy benzene and approximately 18 to 20% by weight of di-(1-phenyl ethyl) butoxy benzene. A trace of 3-(1-phenyl ethyl) butoxy benzene was also detected.

80–82% Styrenated n-butoxy benzene

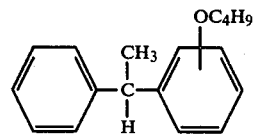

and 18 to 20% Distyrenated butoxy benzene.

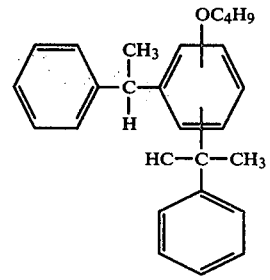

EXAMPLE III

Preparation of the methyl ether of alpha-methyl styrenated phenol

Anisole, 189 grams (1.75 moles), was charged into a glass reactor, equipped with stirrer, thermometer, condenser and dropping funnel. The reactor was blanketed with nitrogen. Borontrifluoride etherate, 1 ml, was charged into the reactor. Temperature of the reactor was raised to 125° C. Alpha-methyl styrene, 109.3 grams (0.926 moles), was added dropwise at 125° C. Temperature of the reactor was maintained at 125° C. until refractive index was constant (1.5511). This required about 2 hours. After cooling to 70° C., 3 ml of 28% aqueous ammonia solution was added. Unchanged anisole was distilled off under vacuum (100 mm) allowing reactor temperature to reach 150° C. The reactor was cooled to room temperature and the product filtered. 92 Grams of recovered anisole and 197 grams of product, composed chiefly of 2- and 4-(1-methyl-1-phenyl ethyl) methoxy benzene was obtained. Refractive index, 25° C., 1.5692, viscosity, 25° C., 21 centipoises.

EXAMPLE IV

Preparation of benzyl anisole

Anisole, 324 grams (3.0 moles) was charged into a glass reactor, equipped with stirrer, thermometer, dropping funnel and condenser from which a tube was extended leading to a trap containing 300 ml of water. The reactor contents were blanketed with nitrogen and catalyst (ferric chloride hexahydrate, 2 grams) was added. The temperature was raised to 60° C. Benzyl chloride, 126 grams (1.0 mole) was added dropwise while maintaining the temperature in the reactor at 60°–65° C. Evolving hydrogen chloride gas was absorbed in the water trap. Progress of the reaction was determined by analysis of the contents of the trap for hydrochloric acid. When the required amount of hydrogen chloride (1 mole) was accounted for, the reaction mixture was cooled to 30° C. Water, 150 grams, was added to dissolve and remove the catalyst. The contents of the reactor were transferred to a separatory funnel to allow the aqueous layer to separate from the organic layer. The lower aqueous layer was then discarded and the organic layer was then washed with a solution of 5 grams sodium carbonate in 150 grams of water followed by a second wash of 150 grams of water. The organic layer was transferred back to the reactor and excess anisole was distilled off under vacuum (15 mm) at 60°–70° C. Weight of recovered anisole was 220 grams. The product was then cooled to 30° C. and filtered through a 1-2 micron porosity filter pad at 20 p.s.i. of nitrogen to obtain 178 grams of material having a refractive index at 25° C. of 1.5818 and a viscosity at 25° C., of 11 centipoises using a Brookfield Viscometer with a #1 spindle at 60 rpm. Gas chromatographic analysis of the product indicated a mixture of materials composed primarily of mono (o, m and p) benzyl anisole and dibenzyl anisole in a ratio of 83.7% to 16.3% by weight respectively.

In the following example, the effect of several solvents upon color development is given. A color development time of 180 seconds or less is considered satisfactory.

EXAMPLE V

The general procedure was as follows.

Two grams of a color former were dissolved in 100 grams of solvent. The resulting solution was applied to a porous surface which was paper toweling. Using a rubber stamp, the solution containing the color former was transferred to the coated side of a sheet of acid clay coated paper. The time required for full color development was measured. The data obtained using this procedure is set forth below.

EXAMPLE VI

The following odor test was conducted. A panel of 25 people was asked to evaluate the odor of the methyl ether of styrenated phenol against benzyl ethyl benzene, a commercial solvent for the color former. Each member of the panel was allowed to sniff containers containing the solvents. Twenty members of the panel found the methyl ether of styrenated phenol to have a less objectionable odor.

EXAMPLE VII

To 100 grams of the methyl ether of styrenated phenol, as prepared in Example I, was added 3.0 grams of Crystal Violet Lactone color former. The mixture was heated to 90° C. with stirring to dissolve the color former and then cooled to 50° C. Separately, a solution containing 20 grams gum arabic, 5 grams of a polyoxyalkylene glycol mono-butyl ether emulsifying agent (Tergitol XD) and 180 grams of water was prepared by stirring and heating to 50° C. To this was added the solution containing the color former. The mixture of the two solutions was stirred at 50° C. until the solvent containing the color former was emulsified. Then, a solution of 20 grams gelatin in 300 grams of water was prepared by slowly adding gelatin to the water at 50° C. The resulting solution was added to the emulsified solvent containing the color former, Crystal Violet Lactone. The resulting mixture was maintained at 50° C. with stirring while 335 grams of water was added dropwise in about 30 minutes. The mixture was then cooled to 10° C., 10 grams of 37% by weight of formaldehyde in water added and the pH adjusted to 9.5 by dropwise addition of a 5% by weight solution in water of sodium hydroxide. This mixture was stirred at 10° C. for about 30 minutes and then allowed to stand overnight at room temperature.

The resulting encapsulated solvent/color former solution was spread on a sheet of uncoated publication paper by means of a No. 8 Meyer spreader. After drying, the coated paper was tested as follows:

The sheet coated with the encapsulated color former was placed, coated side down, against the coated side of acid clay coated paper. When writing on the uncoated side of the sheet containing the encapsulated color former, an image appeared immediately on the sheet bearing the acid clay coating. There was no release of odor resulting from the rupture of the capsules.

EXAMPLE VIII

To 100 grams of the n-butyl ether of styrenated phenol, as prepared in Example II, was dissolved 3.0 grams of Crystal Violet Lactone by stirring and heating to 90° C. The resulting solution was emulsified and encapsulated according to the procedure of Example VII. The resulting encapsulated composition was spread on to a sheet of uncoated publication paper using a No. 8 Meyer spreader. After drying, this coated sheet was tested by placing it, coated side down, against the coated side of acid clay coated paper. When writing on

| SOLVENT | COLOR FORMER | COLOR DEVELOPMENT TIME (SECONDS) |
|---|---|---|
| Methyl ether of styrenated phenol (From Example I) | Crystal violet lactone | 55 |
| Butyl ether of styrenated phenol (From Example II) | Crystal violet lactone | 131 |
| Methyl ether of alpha-methyl styrenated phenol (From Example III) | Crystal violet lactone | 71 |
| Benzyl anisole (From Example IV) | Crystal violet lactone | 40 |
| Ditolylethane (Standard) | Crystal violet lactone | 89 | he uncoated face of the sheet containing the encapsulated color former, an image immediately formed on the acid clay coated paper. No objectionable odor was emitted.

EXAMPLE IX

To 100 grams of the methyl ether of alpha-methyl styrenated phenol as prepared in Example III, was dissolved 3.0 grams of Crystal Violet Lactone by stirring and heating to 90° C. The resulting solution was emulsified and encapsulated according to the procedure of Example VII. The resulting encapsulated composition was spread on a sheet of uncoaed publication paper using a No. 8 Meyer spreader. After drying, this coated sheet was tested by placing it, coated side down, against the coated side of acid clay coated paper. By writing on the uncoated face of the sheet containing the encapsulated color former, an image immediately formed on the acid clay coated paper. No objectionable odor was emitted.

EXAMPLE X

To 100 grams of benzyl anisole as prepared in Example IV, was dissolved 3.0 grams of Crystal Violet Lactone by stirring and heating to 90° C. The resulting solution was emulsified and encapsulated according to the procedure of Example VII. The resulting encapsulated composition was spread on a sheet of uncoated publication paper using a No. 8 Meyer spreader. After drying, this coated sheet was tested by placing it, coated side down, against the coated side of acid clay coated paper. By writing on the uncoated face of the sheet containing the encapsulated color former, an image immediately formed on the acid clay coated paper. No objectionable odor was emitted.

The following example demonstrates the effect of water upon the solvent to reduce odor.

EXAMPLE XI

The solubility of water in the alkoxy diphenyl alkane solvent prepared according to Example I is about 0.4 gram per 100 ml.

A 100 ml sample of the solvent of Example I was placed in a stoppered glass vessel. A quantity of water, 0.35 grams, was then dissolved in the solvent. As a control, another 100 ml sample of the solvent of Example I was placed in another vessel of the same kind. No water was added. A panel of twenty-five individuals was asked to evaluate the odor of the two samples. Each member of the panel was allowed to sniff the two vessels. Twenty-five out of twenty-five members of the panel concluded that the solvent with added water had a milder odor and the quality of the odor was less objectionable.

Additional examples of alkoxy diphenyl alkanes which are useful as solvents for the color former are one or a mixture of the following: 1-benzyl-2,4-dimethoxybenzene; benzyl p-dimethoxybenzene; bis(3,4-dimethoxyphenyl) methane (m.p. 70°–71° C.; 1-benzyl-2,4-dipropoxy benzene; 1-benzyl-2,4-diethoxybenzene; 1-benzyl-2,4-dibutoxybenzene; 1-phenylethyl-2,4-dimethoxybenzene; 3,4-dimethoxyphenyl-3-methoxyphenyl methane (m.p. 45°–46° C.); 1-(3,4-dimethoxyphenyl)-1-phenyl propane; 2-methyl-1-(3,4-dimethoxyphenyl)-1-phenyl propane; 1-(3,4-dimethoxyphenyl)-1-phenyl pentane; 3-methyl-1-(3,4-dimethoxyphenyl)-1-phenyl butane; 3,4-dimethoxyphenyl-3-methylphenyl methane; 3,4-dimethoxyphenyl-3-methoxyphenyl methane; 1-(3,4-dimethoxyphenyl)-1-(4-methylphenyl) ethane; 1-(3,4-dimethoxyphenyl)-1-(4-methoxyphenyl) ethane; 1-(3,4-dimethoxyphenyl)-1-phenyl ethane.

While the invention has been described in detail and with reference to specific embodiments thereof, it will be apparent that various changes and modifications can be made therein which are within the full intended scope of the appended claims.

What is claimed is:

1. Pressure sensitive recording sheets characterized by a more tolerable odor comprising a support having coated thereon a layer of color former, said color former dissolved in a solvent, the improvement wherein said solvent comprises at least one alkoxy diphenyl alkane having the following structure:

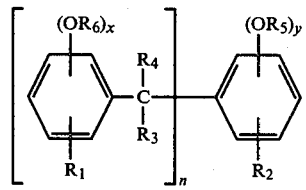

where $R_1$, $R_2$, $R_3$ and $R_4$ are H or a straight or branched chain alkyl group of 1 to 8 carbon atoms and can be the same or different; $R_5$ is a straight or branched chain alkyl group of 1 to 9 carbon atoms; $R_6$ is a straight or branched chain alkyl group of 1 to 8 carbon atoms; x is 0, 1 or 2; y is 1 or 2 and n is 1 or 2, with the proviso that the sum of the carbon atoms in $R_1$, $R_2$, $R_3$, $R_4$, $R_5$ and $R_6$ does not exceed 9 and with the further proviso that where said alkoxy diphenyl alkane is a solid to viscous liquid, at least one diluent or at least one other generally liquid solvent or mixture thereof is present.

2. Pressure sensitive recording paper of claim 1 wherein said alkoxy diphenyl alkane is the methyl ether of styrenated phenol.

3. Pressure sensitive recording sheets of claim 1 wherein said alkoxy diphenyl alkane is a composition containing about 63.6 percent by weight of methyl ether of styrenated phenol, 33.4 percent by weight of methyl ether of distyrenated phenol and about 3.0 percent by weight of higher condensates.

4. Pressure sensitive recording sheets of claim 1 wherein said alkoxy diphenyl alkane is the butyl ether of styrenated phenol.

5. Pressure sensitive recording sheets of claim 1 wherein said alkoxy diphenyl alkane is the methyl ether of alpha methyl styrenated phenol.

6. Pressure sensitive recording sheets of claim 1 wherein said color former is present in an amount of about 1 percent to about 10 percent by weight based on the weight of solvent.

7. Pressure sensitive recording sheets of claim 1 wherein said color former is present in an amount of about 2 percent to about 5 percent by weight based on the weight of solvent.

8. Pressure sensitive recording sheets of claim 1 wherein said color former and solvent are present in microcapsules.

9. Pressure sensitive recording sheets of claim 1 wherein a diluent for said alkoxy diphenyl alkane is present.

10. Pressure sensitive recording sheets of claim 1 wherein a generally liquid solvent in addition to said alkoxy diphenyl alkane is present.

11. Pressure sensitive recording sheets of claim 1 wherein water is present along with said alkoxy diphenylalkane and color former.

12. In a pressure sensitive recording sheet assembly characterized by a more tolerable odor comprising a support having coated thereon a layer of color former dissolved in a solvent and a developer for said color former capable of developing color upon reacting with said color former, the improvement wherein said solvent comprises at least one alkoxy diphenyl alkane having the following structure:

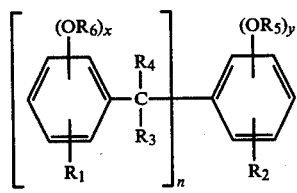

where $R_1$, $R_2$, $R_3$ and $R_4$ are H or a straight or branched chain alkyl group of 1 to 8 carbon atoms and can be the same or different; $R_5$ is a straight or branched chain alkyl group of 1 to 9 carbon atoms; $R_6$ is a straight or branched chain alkyl group of 1 to 8 carbon atoms; x is 0, 1 or 2; y is 1 or 2 and n is 1 or 2, with the proviso that the sum of the carbon atoms in $R_1$, $R_2$, $R_3$, $R_4$, $R_5$ and $R_6$ does not exceed 9 and with the further proviso that where said alkoxy diphenyl alkane is a solid to viscous liquid, at least one diluent or at least one other generally liquid solvent or mixture thereof is present.

13. The assembly of claim 12 wherein said alkoxy diphenyl alkane is the methyl ether of styrenated phenol.

14. The assembly of claim 12 wherein said alkoxy diphenyl alkane is a composition containing about 63.6 percent by weight of methyl ether of styrenated phenol, 33.4 percent by weight of methyl ether of distyrenated phenol and about 3.0 percent by weight of higher condensates.

15. The assembly of claim 12 wherein said color former is present in an amount of about 1 percent of about 10 percent by weight based on the weight of solvent.

16. The assembly of claim 12 wherein said color former is present in an amount of about 2 percent to about 5 percent by weight based on the weight of solvent.

17. The assembly of claim 12 wherein said color former and solvent are present in microcapsules.

18. The assembly of claim 12 wherein a diluent for said alkoxy diphenyl alkane is present.

19. The assembly of claim 12 wherein a generally liquid solvent in addition to said alkoxy diphenyl alkane is present.

20. The assembly of claim 12 wherein water is present along with said alkoxy diphenyl alkane and color former.

* * * * *